United States Patent [19]

Eisum

[11] Patent Number: 5,672,319
[45] Date of Patent: Sep. 30, 1997

[54] DEVICE FOR ANALYZING A FLUID MEDIUM

[75] Inventor: Niels Eisum, Risskkov, Denmark

[73] Assignees: Danfoss A/S, Nordborg, Denmark; Tecator AB, Hoganas, Sweden

[21] Appl. No.: 535,048

[22] PCT Filed: Apr. 28, 1994

[86] PCT No.: PCT/DK94/00171

§ 371 Date: Oct. 10, 1995

§ 102(e) Date: Oct. 10, 1995

[87] PCT Pub. No.: WO94/25876

PCT Pub. Date: Nov. 10, 1994

[51] Int. Cl.$^6$ ............... B01D 61/28; C02F 1/44; G01N 35/08

[52] U.S. Cl. ............. 422/82.02; 422/82.03; 422/82.05; 436/52; 436/63; 204/409; 204/415

[58] Field of Search ............. 422/82, 82.02, 422/82.03, 82.05, 88, 93, 81; 204/409, 415, 400, 401, 403, 416, 417; 436/52, 63

[56] References Cited

U.S. PATENT DOCUMENTS

| | | | |
|---|---|---|---|
| 2,896,459 | 7/1959 | Jemison et al. | 74/60 |
| 3,495,943 | 2/1970 | Kapff | 436/101 |
| 3,635,564 | 1/1972 | Zuckerman et al. | 356/128 |
| 5,087,574 | 2/1992 | Bell et al. | 436/120 |
| 5,238,853 | 8/1993 | Calzi et al. | 436/68 |
| 5,244,561 | 9/1993 | Calzi et al. | 204/415 |
| 5,296,374 | 3/1994 | Culshaw et al. | 435/288 |
| 5,356,819 | 10/1994 | Ritschel | 436/147 |
| 5,401,376 | 3/1995 | Foos et al. | 204/415 |
| 5,457,313 | 10/1995 | Baylor et al. | 250/227.21 |

*Primary Examiner*—Harold Pyon
*Attorney, Agent, or Firm*—Lee, Mann, Smith, McWilliams, Sweeney & Ohlson

[57] ABSTRACT

A fully functional analyzing unit is included within the fluid tight housing of a dialyzer which is immersed in the medium to be analyzed. An opening in the housing is closed by a dialysis membrane. A channel defining body cooperates with the membrane to define a flow channel. The unit includes a carrier fluid reservoir and a carrier pump for generating a flow of carrier fluid through the flow channel. By dialysis via the membrane, the flow of carrier fluid is transformed into a flow of sample fluid. A detecting device is coupled to detect an analyte in the sample fluid and for generating a corresponding detection signal. Effluent sample fluid is received in a waste reservoir. The device is suitable for in situ real-time measurement of plant nutrient salts in process waters of waste water treatment plants.

9 Claims, 3 Drawing Sheets

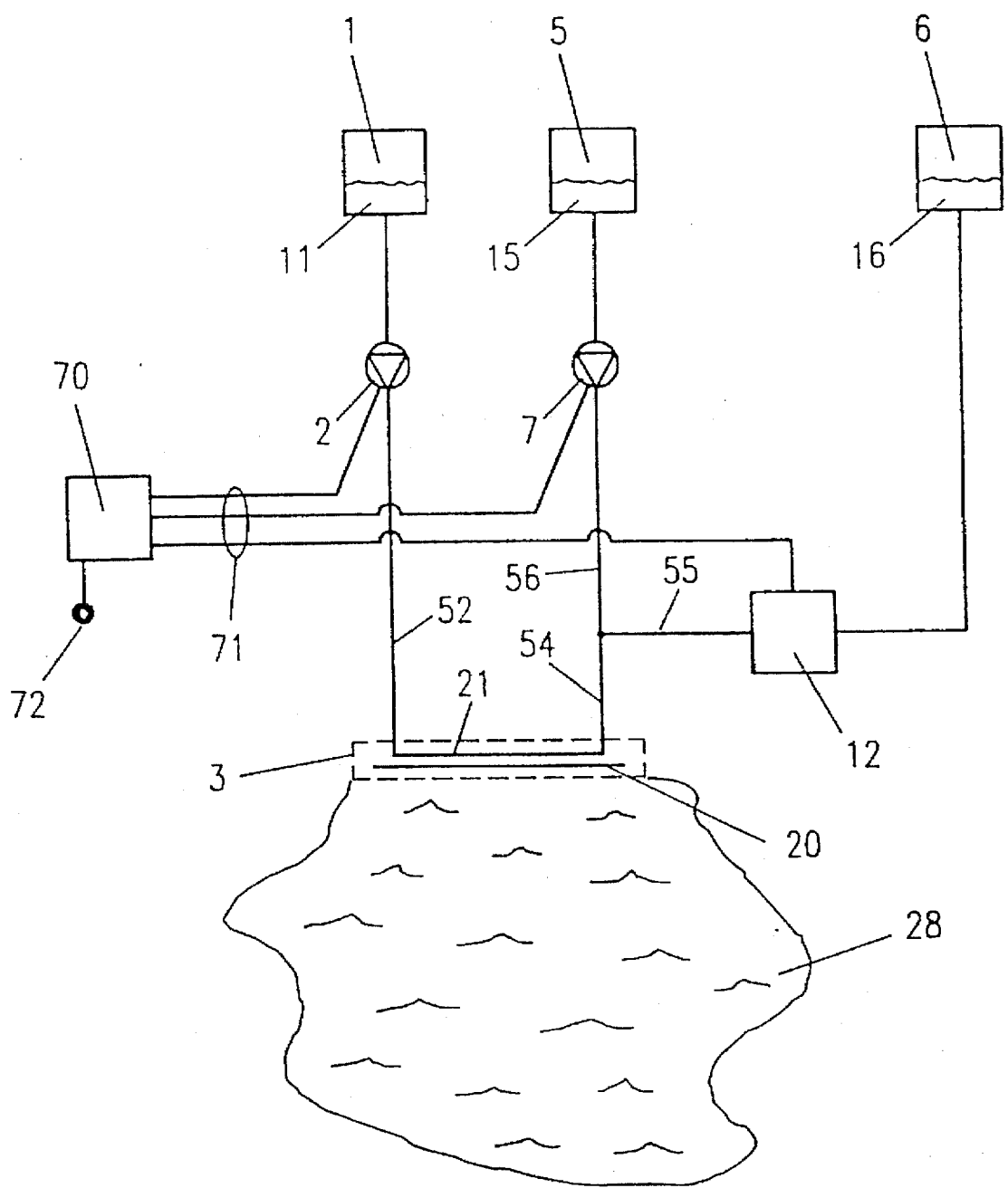

DEVICE FOR ANALYZING A FLUID MEDIUM

The present invention relates to a device for analyzing a fluid medium, in particular a liquid.

Fluid analyzers may be used for controlling chemical and biological processes such as the treatment of sewage water. It is desirable, for example, to lower the concentrations of nutritive salts, such as nitrogen salts, in the effluent from waste water treatment plants. Proper control of the biological processes in the plant is required. It is therefore advantageous to be able to measure the concentrations of the different kinds of ions in the waste water as they, amongst other variables, influence on or inform about the biological processes.

Numerous patents deal with the object of analyzing fluids, especially liquids, for the presence of various analytes. The measurement methods can in principle be divided into three groups:

(1) Methods in which a sample is taken out discontinually, filtered and analyzed;

(2) On-line methods; methods in which a sample is pumped continually out of the bulk process fluid, filtered and then at regular intervals automatically analyzed;

(3) Methods being carried out in situ. Sampling and analyzing gear is entirely or partly immersed in the medium to be analyzed, or sampling is direct and analysis is carried out so close to the process, that the time between a sampling and the development of the analysis result is short enough to allow reliable, real-time control of the process.

An analyzing system for use in process control applications should enable the user to take immediate precautions; for example in waste water treatment, precautions against a suddenly increasing content of nitrate in the fluid medium. The methods in group (1) however are predominantly carried out in the laboratory which inevitably entails a delay in time from sample collection to actual analysis.

Moreover, as water samples are often analyzed spectrophotometrically, long transfer distances may present a further problem because the continuing biological activity in the samples tends to render them less representative. Even if the samples are transported quickly from the sampling site to the laboratory, the analysis results are somewhat uncertain because of problems relating to background turbidity in the samples.

Group (2) above includes UV measurements as well as ion selective electrodes and segmented flow analysis (SFA). The so-called flow injection analysis (FIA), belongs to group (2) as well as to group (1).

The use of ultraviolet (UV) spectrophotometry for water quality analyzing has not been very successful because of interferences from suspended solids and organic matters in the samples. Thomas et al., Fresenius J. Anal. Chem. 338, 234–237 and 238–240 (1990), have attempted to improve the applicability of the UV method by means of the so-called UV multiwavelength absorptiometry (UVMA) method, the purpose of which is to cancel the background signal and simultaneously compute the concentrations of specific absorbing components which significantly disturb the typical shape of the spectrum. The UVMA method, which is intended for use in connection with nitrate determination in natural water and waste water, does however have the drawback, that it requires ultrafiltration of the samples. A similar principle is exploited and marketed by the firm Dr. Lange GmbH, Germany.

The segmented flow analysis (SFA) method was first described in U.S. Pat. Nos. 2,797,149 and 2,879,141, the basic principle being that the samples to be analyzed are separated from one another by air. A refinement of this technique comprising a fluid handling system is described in U.S. Pat. No. 4,853,336. This system is particularly useful for mixing liquid samples with previously separated processing liquids, such as reagents or diluents, in continuous flow analyzers. The system permits the delayed on-line mixing of different components of an analysis mixture, such as samples with reagents or diluents, as well as mixing and interaction of such components in a single conduit.

The basic FIA principle is outlined in U.S. Pat. Nos. 4,022,575 and 4,224,033. A metered amount of the sample is introduced in a moving liquid carrier flow, constituting a well-defined zone, the volume and geometry of which should be strictly reproducible. The sample zone within the carrier flow is transferred through an analysis module and detected in a suitable detection cell. In FIA the sample may be introduced directly in a predetermined amount, optionally using a valve, or it may be introduced using a system of magnetic valves, see e.g. U.S. Pat. No. 4,177,677.

Flow injection analysis requires that sample volumes be metered with great accuracy. This problem is addressed in EP published application 107 631 which describes integrated microconduits for flow analysis wherein a miniaturized system of channels is formed in a monolithic structure. A channel section is designed to be switchable between flow paths, thus allowing the metering of a sample volume by placing it in the switchable channel section while switched into sample flow, and then switching the channel section into analysis flow to process the sample volume in a batch process.

Drawbacks wich are similar to both SFA and FIA are their use of chemicals to create a detectable reaction product, and as a consequence of that the response time for these methods is normaly longer than that for a measuring principle not using chemical reaction before measurement. Furthermore the used chemicals are often poisonous or in other aspects unwanted in the environment and therefore it is preferable to avoid the use of such.

In general a major drawback for the group 2 mentioned above is that there is a response time delay first caused by the used pumps due to the distance from the process to the instrumentation equipment and next by the ultrafiltration system.

An example of an arrangement belonging to group (3) as defined above is a polarography cell, the so-called Clark cell, for direct measurement of the proportional quantity of a substance in a composition. This is described in U.S. Pat. No. 2,913,386. The cell includes a tubular body having a membrane-covered cavity wherein an anode and a cathode are arranged in a predetermined fixed spatial relation. The cavity is filled with an electrolyte. The space between the electrodes defines a "bridge" through which ions are transferred while chemical reactions take place in the electrolyte. The electrolyte is consumed in the chemical reaction and needs to be replaced frequently. The cell is suited to determine e.g. oxygen, $SO_2$ or $CO_2$ in liquids, gases or solids.

A further example belonging to group (3) above is an analyzer designated APP (Automatic Pump Photometer) which has been constructed by ME Meerestechnik-Elektronik GmbH, see the document DE C1 38 22 788. This device is specifically designed for in situ use in water to take samples, analyze the samples directly and store the results of the measurements. The APP analyzer is able to detect changes in concentrations of given substances within relatively short intervals (10–30 min.), the measurable substances being e.g. ammonium, nitrate, nitrite, phosphate, silicate, sulfide, cyanide and heavy metals. The central part of the APP analyzer is a reciprocating pump which serves also as a reaction cell and a cuvette and which aspirates the sample as well as the reagents. The liquid passes through a distributing valve, which opens and closes the different ducts for the liquids and determinates the succession of mixing steps. After each measurement the sample-reagent mixture is expelled from the apparatus.

The APP analyzer is based upon drawing a sample into the system but contains no filtration unit capable of keeping out bacteria; there is therefore a risk of bacterial growth inside the analyzer which again may cause biological activity changing the analyte concentration compared with the outside concentration. The sample must be metered precisely which appears to be rather difficult with the shown combination of pump, reaction cell and cuvette. A relatively large reagent consumption per measurement combined with the fastest cycling time (10–30 minutes) results in a time between reagent replacements of about one week. Some of the reagents used may be toxic, and the release of the sample-reagent mixture after each measurement may be a hazard to the environment as well as to the correctness of future measurements.

The present invention relates to a device of the dialyzer type. It comprises a fluid-tight housing having an opening closed by a membrane having a first and a second major surface and allowing transfer of ions and molecules between the surfaces, the first major surface in use contacting the medium to be analyzed, and further includes channel defining means in the housing fitting with the membrane to define at least one flow channel delimited by the second major surface of the membrane and by the channel defining means.

Such a device is known from the document AT 355 546. The document shows a sterilizable dialyzer for use in fermentation tanks, chemical reactors or the like. The dialyzer includes a dialyzer head covered with a dialysis membrane. The head is to be fitted in an opening in the wall of the tank or reactor. Via a feed line and a drain line in the dialyzer a suitable buffer solution is fed along the back side of the membrane while the liquid in the tank or reactor contacts the front side of the membrane. Dialysable substances present in the liquid are dialysed into the buffer solution via the membrane and transported along the drain line to an external analytical instrument or system.

In the invention as specified in claim 1, a fully functional analyzing unit is included within the fluid-tight housing of a dialyzer. The invention thus provides a self-contained unit including a carrier fluid reservoir and a carrier pump for generating a flow of carrier fluid through the flow channel to allow transfer of ions and molecules between the medium and the carrier fluid across the membrane. As a result, the flow of carrier fluid is transformed into a flow of sample fluid. A detecting device is included within the housing for detecting an analyte in the sample fluid and for generating a corresponding detection signal. Downstream of the detecting device a waste reservoir is provided in the housing for taking up the flow of sample fluid.

It should be noted that in the description of this invention, the term "sample fluid" indicates a fluid which results from a process of dialysis. The sample fluid is created by an exchange of ions and molecules via a membrane; the ions and molecules are exchanged between a fluid medium, which is to be analyzed, and a carrier fluid, which is transformed into a sample fluid by the exchange; this is slightly different from common use in the chemical field where "sample" would simply denote a portion of the fluid medium to be analyzed.

This invention avoids or minimizes numerous drawbacks of the prior art. Specifically, the reliance on a process of dialysis minimizes the risk of internal pollution of the analyzing device as well as the risk of pollution of the environment. All fluids consumed and produced in the analysis are contained and retained in reservoirs within the housing. No contaminant particles or organisms will be aspirated which could disturb the measurement or cause clogging. The use of chemicals for cleaning the flow system is not necessary.

The device according to the invention responds very quickly to changes in the composition of the fluid to be analyzed because the analyzing unit is located within the dialyzer housing, that is, very close to the location where the actual sampling by dialysis is performed. The entire device may be immersed in the fluid to be analyzed. Detection is performed on the spot, and a detection signal indicative of the detection result is generated. The signal may be recorded within the housing for later access, such as in a monitoring application, or it may be transmitted out of the housing to a remote location for recording or further processing such as in a process control application.

The device according to the invention practically eliminates deadtime between measurements and minimizes the delay in time between the "sampling" at the membrane and the "measurement" at the detector; the only delay encountered is the time it takes analyte ions and molecules to travel through the flow system until they are detected at the detecting device.

Due to the basic fact that certain ions and molecules can be detected without the additon of chemicals, it is possible to detect these with suitable detection means directly, that is, substantially no treatment at all of the sample flow is needed.

When possible it has been found preferable, as specified in claim 2, to use a detecting device based on optical measurement. The detection means can for instance be based on UV absorption if the analyte ions or molecules absorb light in the UV region.

As specified in claim 3 the detection device can also be based on an electrochemical interaction between ions or molecules in the sample fluid flow; for example the equivalent of a Clark cell may be integrated in the system.

Due to the non-destructive way of detecting the ions and molecules involved in the sample fluid flow it is possible as specified in claim 4 and 5 to make two or more measurements on the same sample fluid flow.

The embodiment of claim 6 is particularly advantageous in process control applications. The possibility of making a valid detection of the reaction product at any time during an extended period of time allows very direct process control. Occasional calibrations may be required, but the time interval between calibrations may be more than an hour. Deadtime between measurements is minimized, and changes in the concentration of the analyte monitored are detected with minimal time delay. Also, the detection, or "sampling" frequency may be adapted to the rate of change in the analyte concentration.

This is in distinction from batch-oriented methods such as SFA or FIA, in which the detectable species arrives at the detecting device in batches, which are separated from one another either by air or by segments of carrier fluid without the detectable species. In the known methods the output signal, or measurement result, of the detecting device takes the form of peaks or measurement phases, which occur when a zone of detectable species passes the detecting device, and which are separated by valleys or deadtime phases, when a zone of air or unloaded carrier fluid passes the detecting device. Detection must be synchronized with the passage of the detectable species, and timing restrictions are unavoidable. In contrast, in the method and the device according to claim 6, substantially no peaks or valleys, or measurement phases and deadtime phases, are observed; the flow of the analyte at the detecting device is nonsegmented and detection may be made at arbitrary times during extended intervals of time.

In other words, the repetition rate of the measurement may in principle be increased arbitrarily, the only inherent limitation being in the operation of the detecting device rather than in the flow system performing the handling of the sample. For example, the detecting device may include an analog-to-digital converter having a limited repetition rate.

On the other hand, the intervals of time mentioned may be very long and comparable to or at least in the same order of magnitude as typical intervals of time over which substantial changes in analyte concentration occur in large-scale chemical or biological processes, that is, in the order of several minutes to several hours. In other words, the intervals of time may be as long as typical time constants of change in the concentration of the analyte to be monitored or measured. Thus major changes in the analyte concentration may be monitored or measured in an uninterrupted fashion.

The device according to the invention practically eliminates deadtime between measurements and minimizes the delay in time between the "sampling" at the membrane and the "measurement" at the detector; the only delay encountered is the time it takes analyte ions and molecules to travel through the flow system until they are detected.

Preferably the average volume flow in the flow channel during operation is less than 100 µl/min, as specified in claim 7. This results in a low carrier consumption.

For practical purposes it is advantageous to make the volume capacity of the waste reservoir sufficient to allow at least 30 days of uninterrupted operation; replacement of the exhausted reservoirs will be required about once a month and may be conveniently planned.

The device according to the invention is especially well-suited for analyzing contaminated water in waste water purification plants as well as natural water streams, but it is also suitable for measurement and control of other fluid processes (fermentation, paper manufacturing processes, etc.). The invention is, however, in no way limited to these particular applications. Any fluid media, gases as well as liquids, may be analyzed.

It has been found that it is possible with the device according to the invention to reduce analysis response time over the known prior art. The response time for the system according to the invention correspond to the time it takes analyte ions or molecules to travel from the medium to be analyzed, via the membrane, through the flow system and to the detector. It is possible to operate the device in situ so that the analyte only has to travel an extremely short distance. For example, the device may be floated in a partly immersed manner on the surface of waste water in a treatment basin. Response time may be one minute or less.

As mentioned before it has been found that a device according to the invention may be constructed to operate for as long as an entire month or even longer in a self-contained fashion and without the necessity of service. The containers holding carrier fluid and waste fluid are all of sufficient size to store the amount of fluid consumed or produced, respectively, over the whole period of uninterrupted operation which may be a month or more. This is possible because in liquid operation, for example, the liquid consumption may be as low as 0.1–5 liters per month including carrier and auxiliary fluids such as cleaning agent and calibration standards. The membrane may have a comparable lifetime if properly selected to be resistant against penetration or invasion by contaminant particles and organisms.

The use of the device according to the invention, as claimed in claim 9, makes it possible to reduce the size of future waste water purification plants considerably because of the quick response of the device to changes in the process conditions which govern the biological processes in waste water treatment plants. Corrective action to any changes may be taken early in time, improving the overall efficiency of the biological processes and thus reducing the size of future plant or, conversely, increasing the treatment capacity of existing plant. At the same time, the amount and cost of chemicals used in water treatment may be reduced.

The principles of the invention will be explained in further detail below. Reference is made to the accompanying drawings in which:

FIG. 1 is a schematic diagram of a flow system according to the invention

FIG. 2b is a cross-sectional view of the sampling cell including the part shown in FIG. 2a;

Figure 2A:
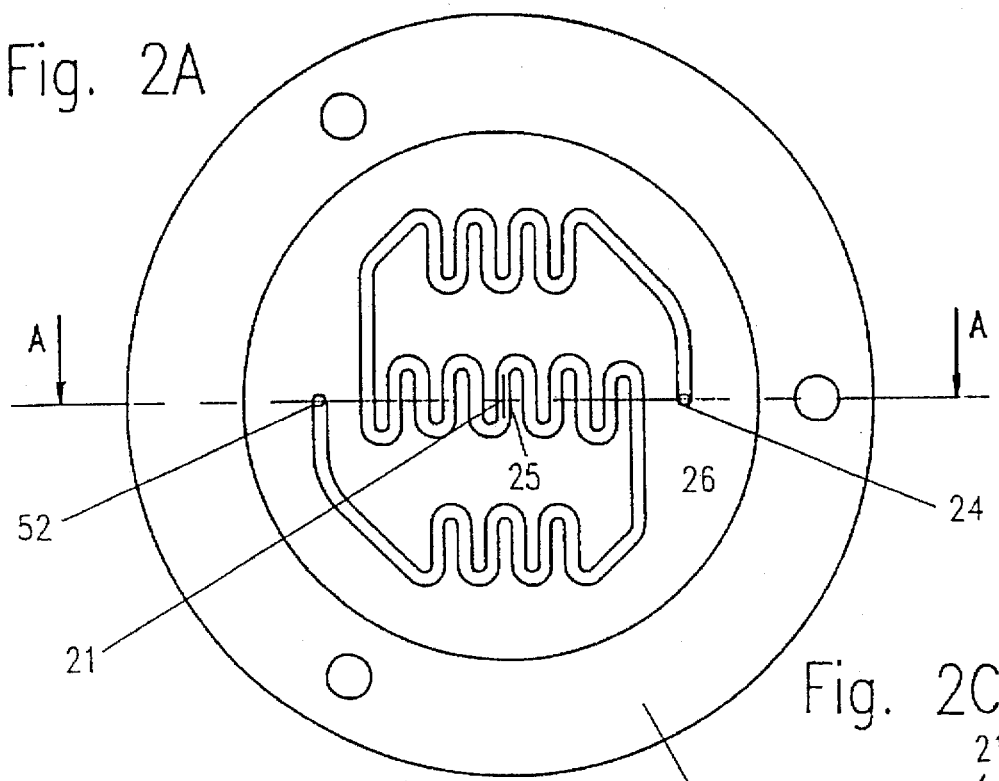
FIG. 2a is a plan view of a part of a sampling cell for use in a flow system as shown in FIG. 1.

FIG. 1 shows the main components of a system according to the invention which is adapted for analyzing for example nitrate in water. The main components are: liquid containers 1, 5, and 6 for various liquids 11, 15 and 16 to be used or produced when the system is working; pumps 2 and 7 both controlled by a controller circuit 70 via wires 71, for pumping the liquids through the analyzing system via channels 52 and 56, a sampling cell 3 with a flow channel 21 and a membrane 20, in use contacting the medium 28 to be analyzed, for generating a sample liquid and a detecting device 12 coupled to the controlling circuit 70. The detection result is signaled to the controlling circuit 70 for display or transmittal via remote signal bus 72.

In FIG. 1 the container 1 contains laboratory-grade demineralized water 11 which is to serve as a carrier liquid. It is however possible to change the carrier liquid. In some measurement specific ions can disturb the measurement due to interferences. As an example, chlorine ions can disturb a nitrate measurement performed by means of an ion selective electrode, that is, the chlorine ions are measured as if they where nitrate ions. These measurement problems can be eliminated by choosing a carrier solution having a content of chemicals being able to bind the interfering ions in a non-disturbing constitution which does not affect the measurement.

Via channel 52 the pump 2 pumps the carrier liquid into the sample generating cell 3. In the cell 3 the carrier liquid is guided trough a flow channel 21 along the back side of the membrane 20. The flow channel is defined or delimited by the back side, or second major surface, of the membrane 20, and by a suitable mechanical device (not shown) in contact with the membrane. The front side, or first major surface, of the membrane 20 is shown to be in direct contact with the medium to be analyzed, i.e. waste water 28.

The membrane 20 is made of a material allowing transfer of ions or molecules across the membrane. This will allow the migration of ions and molecules, including nitrate ions, from the waste water 28 through the membrane and into the flow of carrier liquid 11. As a result, the carrier liquid becomes loaded with ions or molecules from the waste water as it flows along the flow channel 21, which transforms the carrier liquid into a sample liquid leaving the cell 3 and entering the detector via channel 54. Of course, the use of the word "sample" in this instance differs from ordinary use in that the sample liquid in the present flow system is not a physical sample of the waste water, but rather an image of the constitution of the waste water, formed by the specific mechanism of transfer via the membrane 20 which may be diffusion.

As indicated schematically, the channel 55 runs through a detection device 12. This could be an optical instrument, preferably an analytical UV instrument, and in this specific example detection can be done directly by utilizing the fact that nitrate absorbs light in the ultraviolet region. The detection device may, however, also be an IR or NIR instrument or an electrochemical detection instrument, or some other suitable device.

Due to the fact that the content of the sample fluid flow is measured in a non-destructive way (without any addition of chemicals to the sample fluid flow) it is possible to make more than one measurement on the same sample. This may be done by placing one or more additional detectors in series with the detector 12 (this is not shown in the drawings). In a variation of the concept of the invention it may even be possible to avoid the use of a waste reservoir, that is, it may be possible to release the sample flow into the waste water 28 after measurement if no substances are used in the carrier fluid which are hazadous for the process.

The flow system downstream of the sampling cell 3 may be calibrated at any time by using specific reference liquids 15 fed to the detector 12 from container 5 by means of pump 7 operating into channel 56. Pump 2 is stopped while pump 7 is operated, so as to substitute the flow of reference liquid in channel 55 for the flow of sample liquid from sampling cell 3 in channel 54. Otherwise, the device operates in the same way during calibration as explained previously for sample flow. Calibration for the whole of the detecting device is thus achieved by relating the absorbance measured during calibration to the known concentration of the reference liquid 15.

In a similar fashion, the transmission characteristics of the membrane 20 may be accounted for in calibration prior to operation of the device by contacting the membrane 20 with a standard solution of known concentration instead of the waste water 28, operating the system as when measuring waste water, and relating the measured absorbance to the known concentration in the standard solution.

The pumps 2 and 7 are positive displacement pumps and a suitable type of pump is described in U.S. Pat. No. 2,896,459; proper control of pump operation may be achieved by driving it via an electric stepping motor controlled by a suitable control circuit.

The flow system may be cleaned, if necessary, by flushing it with a cleaning solution, not shown on the figure but working in the same way as the calibration procedure. Both calibration and cleaning of the flow system may be performed without removing the device from the analysis site.

Figure 2C:
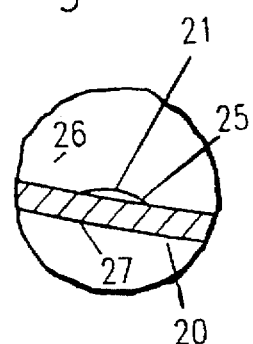
FIG. 2c is a superimposed area of the flow channel 2c in FIG. 2b.
Figure 2B:
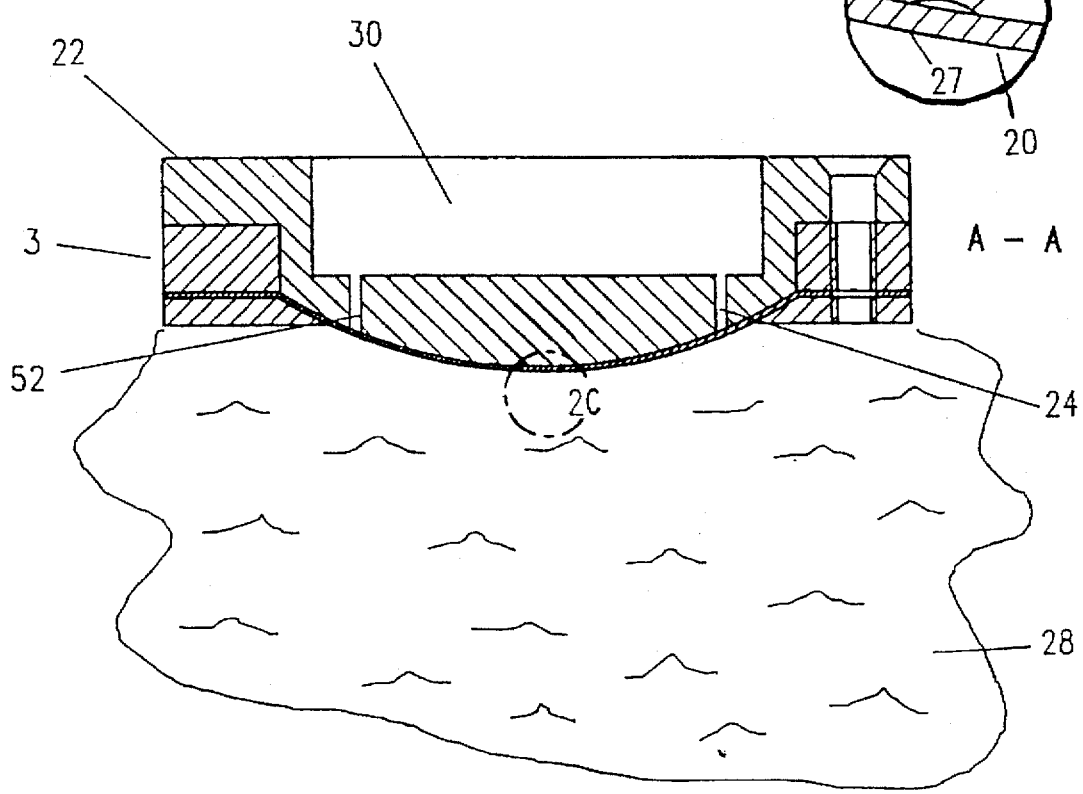

FIGS. 2b and 2c are cross-sectional view of the sample generating cell 3. The cell includes a channel defining means or support 22 fitted with the membrane 20. The support 22 is shaped generally as a disc which is formed with a meandering groove 25 (see FIG. 2a) on a surface 26 adjacent to the membrane 20. Fitted snugly to the membrane 20 as it is in use, the support 22 with groove 25 cooperates with the membrane to define a flow channel 21 of fixed shape and dimensions which is delimited by the back side of the membrane.

The surface 26 of the support 22 on which the recess is formed is hemispherical in shape except for the presence of the groove 25. The membrane 20, on the other hand, is made from plane sheet material and will become tensioned against the hemispherical surface of the support 22 when it is mounted thereon. The tensioning ensures that the membrane will not be lifted off the support 22 by the pressure which prevails in the flow channel 21 when carrier liquid is pumped through it.

If such lift-off were to occur, the various arms of the meandering flow channel 21 might short-circuit through the formation of "wild" flow paths between the membrane and the support. This would entail calibration difficulties because portions of liquid running through the wild flow paths would be in contact with the membrane 20 during a dwelling time which would be different from the dwelling time experienced by liquid portions which travel all along the flow path 21. The effect would be that the "wild" flow has generally less time to be loaded with analyte than the "ordinary" flow, causing an apparent change in the calibration of the cell 3. The convex form of the support 22 and the tensioned membrane prevents this.

The flow channel 21 is shaped to have a rather large surface area covered by the membrane 20, if compared to the volume of the channel. By way of example, the groove may have a semicircular form with a width of about 1 mm and a maximum depth of about 0.13 mm, resulting in a membrane surface area to channel volume ratio of about 11/mm. Even shallower grooves may be attainable depending on the elasticity of the membrane and geometry considerations.

The membrane material is selected among materials which in all essentials only allow transfer of ions and molecules across the membrane. This may be achieved by using a membrane made from an impermeable material and subjecting it to perforation by irradiation (such membranes are commercially available under the trademark Nuclepore, amongst others) which will form very narrow channels in the membrane. Other suitable semipermeable membranes are known to workers in the fields of dialysis and osmosis.

Suitable membrane materials include cellulose acetate, teflon, regenerated cellulose acetate, polycarbonate and polyester. Materials like ceramics, for example $Al_2O_3$, may also be suitable as membrane materials.

Optionally the membrane can be covered with a permeable protective matrix placed in such a way that the protective matrix is contacting the medium to be analyzed, that is, on the front side or first major surface 27 of the membrane. An example of a suitable protective layer is fiber layer such as filtration paper. Such a coverage may prevent abrasion or other detrimental effects brought about by swelling of the membrane in water.

The overall thickness of the membrane is preferably about 5–250 μm, especially about 25 μm. Pores in the membrane are preferably about 0.01–0.45 μm in size, especially about 0.025 μm. This small pore size prevents dirt particles, bacteria, spores of funghi and possibly even large organic molecules from entering the flow system, thus preventing continuing biological activities in the analysis system. It is preferred to select the material of the membrane so as to prevent transfer of particles from the medium to be analyzed which exceed the size of analyte ions or molecules by a factor ten or more.

The support 22 is provided with through-going bores 52 and 24 which connect the flow channel 21 to other parts of the flow system. Bore 52 leads to the pump 2 for delivering carrier liquid 11, and bore 24 leads to channel 54.

The detecting device is mounted in the immediate vicinity of the back side of the channel 54 making it possible to make a instantaneous measurement.

Figure 3:
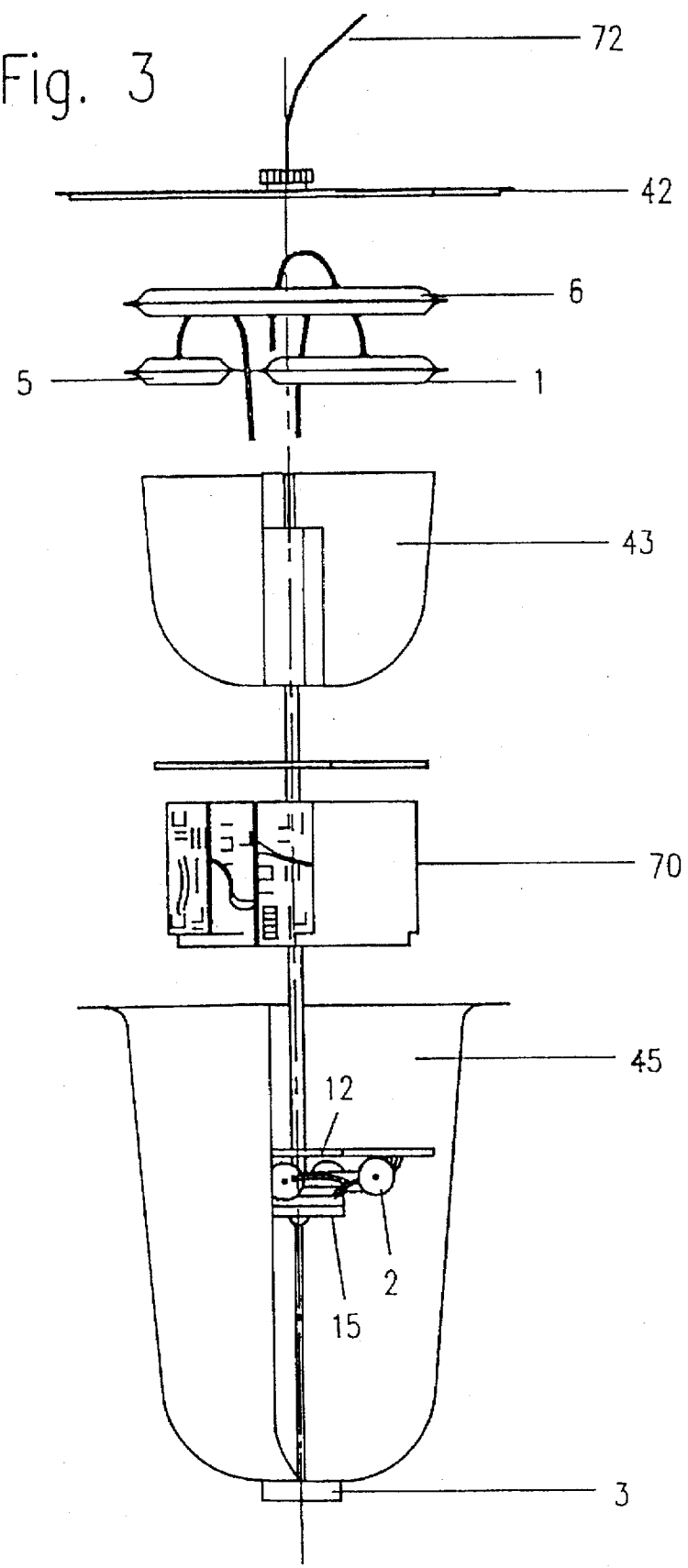
FIG. 3 is an exploded view illustrating the general layout of a self-contained, submersible device according to the invention for performing in situ analysis of waste water.

FIG. 3 illustrates one of many possible ways of housing and partitioning a device according to the invention. The upper part of FIG. 3, immediately just below a lid 42, by way of example shows fluid containers 1, 5 and 6 placed in a compartment 43 to ensure that any leak from the containers does not disturb operation or even damage the rest of the system. The control circuit 70 for controlling the system and for receiving/transmitting input and output signals via remote signal bus 72 is placed below the reagent compartment. Pumps and detector are located below the control circuit 70; the sampling or dialysis cell 3 is fitted in the bottom of a common housing 45 which holds all other parts and may be sealed tighly by the lid 42.

Power supply and all communication (input/output) to the system is via the remote bus 72. An output signal from the system, for example representing the amount af nitrate in waste water read by the detector, could be evaluated in a remote control unit (not shown) coupled to the remote bus 72 for controlling a waste water plant in response to signals from the analysis system. If the amount were too high, the nesssary steps to reduce the amount measured could be initiated at once. In the same way it is possible via remote bus 72 to deliver input signals to the system for example to start a calibration procedure.

I claim:

1. A self-contained, immersible dialyzer for analyzing a fluid medium, especially a liquid, comprising:

a fluid-tight housing;

an opening in the housing, the opening being closed by an ion-permeable membrane, the membrane having a first surface and a second surface and allowing transfer of ions and molecules between the surfaces, the first surface in use comprising an outer surface for contacting the medium;

channel defining means within the housing, the channel defining means being joined to the membrane to define at least one flow channel delimited by the second surface of said membrane and by the channel defining means;

a carrier fluid reservoir within the housing, the carrier fluid reservoir being adapted to hold a carrier fluid;

carrier pump means within the housing, the carrier pump means being operative for generating a flow of carrier fluid through the flow channel to allow transfer of ions and molecules between the medium and the carrier fluid across the membrane as the carrier fluid flows through the flow channel, so as to transform the flow of carrier fluid into a flow of sample fluid;

at least one detecting device within the housing, the detecting device being coupled to the flow of sample fluid for detecting an analyte in the sample fluid and for generating a corresponding detection signal; and at least one waste reservoir within the housing separate from said carrier fluid reservoir, the waste reservoir being located downstream of the detecting device and adapted to receive the flow of sample fluid.

2. A dialyzer as in claim 1, in which the detecting device is an optical device.

3. A dialyzer as in claims 1, in which the detecting device is an electrochemical device.

4. A dialyzer as in claim 1, in which average volume flow in the flow channel during operation is less than 100 µl/min.

5. A dialyzer as in claim 1, in which volume capacity of the waste reservoir is sufficient to allow at least 30 days of uninterrupted operation.

6. The use of a dialyzer as claimed in claim 1 for in situ real-time measurement of plant nutrient salts in process waters of waste water treatment plants.

7. A dialyzer as in claim 1, in which the pump means is operative to generate a substantially continual flow and wherein at least one detecting device is operative to make a valid detection of at least one analyte at any time during an extended period of time.

8. A dialyzer as in claim 11 further comprising a second detecting device, the second detecting device being coupled to the flow of sample fluid downstream of the detecting device first mentioned (hereinafter the first detecting device), for detecting the analyte in the sample fluid and for generating a corresponding second detection signal, wherein the second detecting device operates on a different detection principle than the first detecting device.

9. A dialyzer as in claim 1 further comprising a second detecting device, the second detecting device being coupled to the flow of sample fluid downstream of the detecting device first mentioned (hereinafter the first detecting device), for detecting a second analyte in the sample fluid and for generating a corresponding second detection signal.

* * * * *